US006028216A

United States Patent [19]
Morales et al.

[11] Patent Number: 6,028,216
[45] Date of Patent: Feb. 22, 2000

[54] ASYMMETRIC SYNTHESES AND INTERMEDIATES FOR PREPARING ENANTIOMER-ENRICHED HYDROXYPHOSPHINYL DERIVATIVES

[75] Inventors: Guillermo Morales, Edgewood; Weixing Li, Baltimore; Paul F. Jackson, Bel Air, all of Md.

[73] Assignee: Guilford Pharmaceuticals Inc., Baltimore, Md.

[21] Appl. No.: 09/002,146

[22] Filed: Dec. 31, 1997

[51] Int. Cl.$^7$ ........................................................ C07F 9/30
[52] U.S. Cl. ............................... 562/24; 546/21; 546/22; 548/412; 548/414; 549/6; 549/216; 549/218
[58] Field of Search ................................................. 562/24

[56] References Cited

U.S. PATENT DOCUMENTS

| | | |
|---|---|---|
| H1312 | 5/1994 | Coughlin et al. . |
| 4,151,172 | 4/1979 | Ondetti et al. . |
| 4,168,267 | 9/1979 | Petrillo, Jr. . |
| 4,316,896 | 2/1982 | Thorsett et al. . |
| 4,337,201 | 6/1982 | Petrillo, Jr. . |
| 4,374,131 | 2/1983 | Petrillo, Jr. . |
| 4,444,765 | 4/1984 | Karanewsky et al. . |
| 4,448,772 | 5/1984 | Karanewsky . |
| 4,452,790 | 6/1984 | Karanewsky et al. . |
| 4,452,791 | 6/1984 | Ryono et al. . |
| 4,468,519 | 8/1984 | Krapcho . |
| 4,547,324 | 10/1985 | Wong et al. . |
| 4,555,506 | 11/1985 | Karanewsky et al. . |
| 4,560,680 | 12/1985 | Ryono et al. . |
| 4,560,681 | 12/1985 | Karanewsky . |
| 4,567,166 | 1/1986 | Karanewsky et al. . |
| 4,616,005 | 10/1986 | Karanewsky et al. . |
| 4,671,958 | 6/1987 | Rodwell et al. . |
| 4,703,043 | 10/1987 | Karanewsky et al. . |
| 4,715,994 | 12/1987 | Parsons et al. . |
| 4,716,155 | 12/1987 | Karanewsky et al. . |
| 4,741,900 | 5/1988 | Alvarez et al. . |
| 4,849,525 | 7/1989 | Weller, III et al. ..................... 548/413 |
| 4,853,326 | 8/1989 | Quash et al. . |
| 4,867,973 | 9/1989 | Goers et al. . |
| 4,885,283 | 12/1989 | Broadhurst et al. . |
| 4,906,779 | 3/1990 | Weber et al. . |
| 4,918,064 | 4/1990 | Cordi et al. . |
| 4,937,183 | 6/1990 | Ultee et al. . |
| 4,950,738 | 8/1990 | King et al. . |
| 4,959,493 | 9/1990 | Ohfune et al. . |
| 4,962,097 | 10/1990 | Parsons et al. . |
| 4,966,999 | 10/1990 | Coughlin et al. . |
| 4,988,681 | 1/1991 | Ishikawa et al. . |
| 4,994,446 | 2/1991 | Sokolovsky et al. . |
| 5,030,732 | 7/1991 | Morita et al. . |
| 5,041,644 | 8/1991 | Morita et al. . |
| 5,047,227 | 9/1991 | Rodwell et al. . |
| 5,061,806 | 10/1991 | Morita et al. . |
| 5,093,525 | 3/1992 | Weber et al. . |
| 5,099,063 | 3/1992 | Parsons et al. . |
| 5,136,080 | 8/1992 | Miller et al. . |
| 5,140,104 | 8/1992 | Coughlin et al. . |
| 5,143,908 | 9/1992 | Parsons et al. . |
| 5,145,990 | 9/1992 | Parsons et al. . |
| 5,147,867 | 9/1992 | Parsons et al. . |
| 5,156,840 | 10/1992 | Goers et al. . |
| 5,162,504 | 11/1992 | Horoszewicz . |
| 5,162,512 | 11/1992 | King et al. . |
| 5,190,976 | 3/1993 | Weber et al. . |
| 5,196,510 | 3/1993 | Rodwell et al. . |
| 5,242,915 | 9/1993 | Ueda et al. . |
| 5,262,568 | 11/1993 | Weber et al. . |
| 5,326,856 | 7/1994 | Coughlin et al. . |
| 5,336,689 | 8/1994 | Weber et al. . |
| 5,449,761 | 9/1995 | Belinka, Jr. et al. . |
| 5,474,547 | 12/1995 | Aebischer et al. . |
| 5,489,525 | 2/1996 | Pastan . |
| 5,495,042 | 2/1996 | Belinka, Jr. et al. . |
| 5,500,420 | 3/1996 | Maiese . |
| 5,508,273 | 4/1996 | Beers et al. . |
| 5,527,885 | 6/1996 | Coughlin et al. . |
| 5,538,866 | 7/1996 | Israeli et al. . |
| 5,538,957 | 7/1996 | Tsaklakidis et al. . |
| 5,698,402 | 12/1997 | Luderer et al. . |

FOREIGN PATENT DOCUMENTS

| | | |
|---|---|---|
| 2210043A | 6/1989 | United Kingdom . |
| WO 96/26272 | 8/1996 | WIPO . |

OTHER PUBLICATIONS

Akutagawa, S. Asymmetric synthesis by metal BINAP catalysts. Applied Catalysis A. General, 128, 171–207 (1995), 1995.

Coover, H.W., "Reaction of Triethyl Phosphite with 2–halocrylates" *Journal of the American Chemical Society*, 79:2, 1957, p. 1963–1966 (Jun. 29, 1956).

Khairullin, V.K., et al. "Reaction of Ethylphosphonous Dichloride with α,β–unsaturated acids" *Chemical Abstracts*, (1966) Abstract No. 64:11, Zh. Obshch, Khim. (1966), 36(2), 296–302 (Russ).

Yuanyao Xu and Zhong Li, "Palladium–Catalysed Synthesis of Alkyl Alkenylmethyl and Alkenylphenylphosphinates" *Synthesis*, p. 240–242 (Mar. 1986).

Sainz–Diaz, Claro I., et al. "Synthesis and Molecular Structure of Carboxyalkenylphosphonic, and Alkenylbisphosphonic Derivatives" *New J. Chem.* 20:11, p. 1195–1211 (Jan. 12, 1996).

Stauch, B. et al., "The effects of N–acetylated alpha linked acidic dipeptidase (NAALADase) inhibitors on [$^3$H]NAAG catabolism in vivo," *Neuroscience Letters*, 100, p. 295–300 (1989).

Subasinghe, N. et al., "Synthesis of Acyclic and Dehydroaspartic Acid Analogues of Ac–Asp–Glu–OH and Their Inhibition of Rat brain N–acetylated α–linked Acidic Dipeptidase (NAALA Dipeptidase)," *J. Med. Chem.*, 33, p. 2734–2744, (1990).

(List continued on next page.)

*Primary Examiner*—Michael G. Ambrose
*Attorney, Agent, or Firm*—Nath & Associates; Gary M. Nath; Suet M. Chong

[57] ABSTRACT

The present invention relates to asymmetric syntheses and intermediates for preparing enantiomer-enriched hydroxyphosphinyl derivatives.

13 Claims, No Drawings

OTHER PUBLICATIONS

Rothstein, J. et al., "Abnormal excitatory amino acid metabolism in amyotrophic lateral sclerosis," *Anals of Neurology*, vol. 28, p. 18–25 (1990).

Slusher, B. et al., "Rat brain N-acetylated α–linked acidic dipeptidase activity," *The J. of Biological Chemistry*, vol. 265, No. 34, p. 21297–21301, (1990).

Tsai, G. et al., "Reductions in acidic amino acids and N–acetylaspartylglutamate in amyotrophic lateral sclerosis," *Brain Research*, 556, p. 151–161 (1991).

Coyle, J. et al., "N–acetyl–aspartyl glutamate," *Excitatory Amino Acids*, p. 69–77 (1990).

Meyerhoff, J. et al., "Genetically epilepsy–prone rats have increased brain regional activity of an enzyme which liberates glutamate from N–acetyl–aspartyl–glutamate," *Brain Research*, 593, p. 140–143 (1992).

Meyerhoff, J. et al., "Activity of a NAAG–hydrolyzing enzyme in brain may affect seizure susceptibility in genetically epilepsy–prone rats," *Molecular Neurobiology of Epilepsy*, p. 163–172 (1992).

Slusher, B. et al., "Immunocytochemical localization of the N–acetyl–aspartyl–glutamate (NAAG) hydrolyzing enzyme N–acetylated α–linked acidic dipeptidase (NAALADase)," *J. of Comp. Neurology*, 315, p. 217–229 (1992).

Tsai, G. et al., "Immunocytochemical distribution of N–acetylaspartylglutamate in the rat forebrain and glutamergic pathways," *J. of Chem. Neuroanatomy*, 6, p. 277–292 (1993).

Tsai, G. et al., "Changes of excitatory neurotransmitter metabolism in schizophrenic brains," *Salmon Lecturer of the New York Academy of Medicine*, (Dec. 2–3, 1993).

Slusher, B. et al., "NAALADase: A Potential Regulator of Synaptic Glutamate," *Biotech Update DuPont NEN*, 9, p. 37–39 (1994).

Koenig, M. et al., "N–acetyl–aspartyl–glutamate (NAAG) elicits rapid increase in intraneuronal $Ca^{2+}$ in vitro," *NeuroReports*, 5, p. 1063–1068 (1994).

Jackson, P. et al., "Design, synthesis, and biological activity of a potent inhibitor of the neuropeptidase N–acetylated α–linked acidic dipeptidase," *J. of Medicinal Chemistry*, (1995).

Vornov, J. et al., "Toxic NMDA–receptor activator occurs during recovery in a tissue culture model of ischemia," *J. of Neurochemistry*, 65, p. 1681–1691 (1995).

Woods, D. et al., "Gender–linked injury after focal cerebral ischemia," *Soc. For Neuroscience 1996 Abstract Form*, (1996).

Bhardwaj, A. et al., "Striatal nitric oxide (NO) production is enhanced in focal cerebral ischemia: An in vivo microdialysis study," *Soc. For Neuroscience 1996 Abstract Form*, (1996).

Heston, W., "Bedeutung des prostataspezifischen Membranantigens (PSMA)," *Urologe*, 35, p. 400–407 (1996).

Carter, R. et al., "Prostate–specific membrane antigen is a hydrolase with substrate and pharmacologic characteristics of neuropeptidase," *Proc. Nat. Acad. Sci.*, 93, p. 749–753 (1996).

ASYMMETRIC SYNTHESES AND INTERMEDIATES FOR PREPARING ENANTIOMER-ENRICHED HYDROXYPHOSPHINYL DERIVATIVES

BACKGROUND OF THE INVENTION

1. Field of the Invention

The present invention relates to asymmetric syntheses and intermediates for preparing enantiomer-enriched hydroxyphosphinyl derivatives.

2. Description of the Prior Art

Asymmetric Syntheses

Asymmetric synthesis is important in the pharmaceutical industry because often only one optically active isomer (enantiomer) has any beneficial therapeutic effect. Such is the case of the non-steroidal anti-inflammatory compound naproxen. The S-enantiomer of naproxen is an effective anti-arthritic drug, while the R-enantiomer is a known liver toxin. The differences in pharmacological effectiveness between two such enantiomers often makes it desirable to selectively synthesize one enantiomer over its mirror image.

It is known in the art that organic syntheses of pharmaceutical compounds often results in optically inactive racemic mixtures Racemic mixtures contain equal amounts of species having optically opposite activities and thereby cancel one another out. In order to obtain the desired enantiomeric compound from racemic mixtures it is necessary to separate the racemic mixture into its optically active components. Separation of enantiomers, known as optical resolution, can be carried out by physical sorting, direct recrystallisation, or other methods known in the art. Such separation methods are often slow, expensive and destructive to the compounds of interest. Because of these inherent problems in separation methods, more effort has been directed to employing asymmetric synthesis where one of the enantiomers is preferentially synthesized in larger amounts.

Accordingly, there is a need for asymmetric syntheses that provide good yields of optically active products and that have high stereoselectivity.

Hydroxyphosphinvl Derivatives

Hydroxyphosphinyl derivatives have recently been found to inhibit N-acetylated α-linked acidic dipeptidase (NAALADase). Such activity has proven to be useful in treating various diseases; conditions and disorders, including glutamate abnormalities (particularly stroke, Parkinson's Disease, Amyotrophic Lateral Sclerosis (ALS), spinal cord injury, alcoholism and nicotine dependence), and prostate diseases (particularly prostate cancer). Since the inhibition of NAALADase by hydroxyphosphinyl derivatives may be highly stereospecific and regiospecific, an enantiomerically pure hydroxyphosphinyl derivative would be desirable for optimal pharmacological activity. However, asymmetric reduction of ethylene substituted phosphoesters has been difficult to achieve. Accordingly, a need exists for new methods of reducing such compounds to synthesize enantiomerically-enriched hydroxyphosphinyl derivatives.

SUMMARY OF THE INVENTION

The present invention relates to a method of synthesizing in non-racemic form a compound of formula I

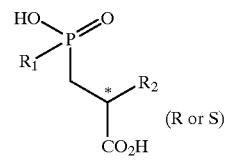

which comprises asymmetrically reducing a compound of formula II

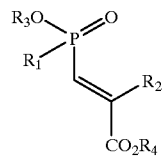

wherein:
$R_1$, $R_2$, $R_3$ and $R_4$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_1$, $R_2$, $R_3$ and $R_4$ are independently unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, and Ar; and Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl, benzyl and phenyl, wherein said Ar is unsubstituted or substituted with one or more substituent(s) independently selected from the group consisting of halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, and amino.

The present invention also relates to an intermediate for such method, namely a compound of formula II

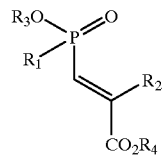

or a pharmaceutically acceptable salt or hydrate thereof, wherein:
$R_1$, $R_2$, $R^3$, and $R_4$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_1$, $R_2$, $R_3$ and $R_4$ are independently unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, and Ar; and Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyrLdyl, 4-pyridyl, benzyl and phenyl, wherein said Ar 1S unsubstituted or substituted with one or more substituent(s) independently selected from the group consisting of halo, hydroxy, alkoxy, $C_2$–$C_6$ alkenyloxy, phenoxy, benzyloxy, and amino.

DETAILED DESCRIPTION OF THE INVENTION

Definitions

"Enantiomers" refer to stereoisomers which are non-superimposable mirror images of one another.

"Stereoisomers" refer to compounds which have identical chemical constitution, but differ as regards the arrangement of the atoms or groups in space.

"Racemic" refers to a mixture containing equal parts of individual enantiomers.

"Non-racemic" refers to a mixture containing unequal parts of individual enantiomers.

"Enantiomer-enriched" refers to a mixture in which one enantiomer predominates.

"Chiral" refers to molecules which have one or more centers of asymmetry.

"Achiral" refers to molecules or processes which do not include or involve at least one center of asymmetry.

"Chiral center" refers to any structural feature of a molecule that is a site of asymmetry.

"Stereoselective" refers to a process which produces a particular stereoisomer in favor of others.

"Optical activity" refers to an indirect measurement of the relative amounts of stereoisomers present in a given product. Chiral compounds have the ability to rotate plane polarized light. When one enantiomer is present in excess over the other, the mixture is optically active.

"Optically active" refers to a mixture of stereoisomers which rotates plane polarized light due to an excess of one of the stereoisomers over the others.

"Optically pure" refers to a single stereoisomer which rotates plane polarized light.

"Regioisomers" refers to compounds which have the same molecular formula but differing in the connectivity of the atoms.

"Regioselective" refers to a process which favors the production of a particular regioisomer.

"Attention Deficit Disorder" refers to a disorder characterized by developmentally inappropriate inattention and impulsivity, with or without hyperactivity. Inattention means a failure to finish tasks started, easy distractibility, seeming lack of attention, and difficulty concentrating on tasks requiring sustained attention. Impulsivity means acting before thinking, difficulty taking turns, problems organizing work, and constant shifting from one activity to another. Hyperactivity means difficulty staying seated and sitting still, and running or climbing excessively.

"Compulsive disorder" refers to any disorder characterized by irresistible impulsive behavior Examples of compulsive disorders include without limitation drug dependence, eating disorders, pathological gambling, ADD and Tourette's syndrome.

"Drug dependence" refers to a psychologic addiction or a physical tolerance to a drug. Tolerance means a need to increase the dose progressively in order to produce the effect originally achieved by smaller amounts.

"Eating disorder" refers to compulsive overeating, obesity or severe obesity. obesity means body weight of 20% over standard height-weight tables. Severe obesity means over 100% overweight.

"Glutamate abnormality" refers to any disease, disorder or condition in which glutamate is implicated, including pathological conditions involving elevated levels of glutamate. Examples of glutamate abnormalities include epilepsy, stroke, Alzheimer's disease, Parkinson's Disease, Amyotrophic Lateral Sclerosis (ALS), Huntington's Disease, schizophrenia, chronic pain, ischemia, neuronal insult and compulsive disorders.

"Inhibition", in the context of enzymes, refers to reversible enzyme inhibition such as competitive, uncompetitive and non-competitive inhibition. Competitive, uncompetitive and non-competitive inhibition can be distinguished by the effects of an inhibitor on the reaction kinetics of an enzyme. Competitive inhibition occurs when the inhibitor combines reversibly with the enzyme in such a way that it competes with a normal substrate for binding at the active site. The affinity between the inhibitor and the enzyme may be measured by the inhibitor constant, $K_i$, which is defined as:

$$K_i = \frac{[E][I]}{[EI]}$$

wherein [E] is the concentration of the enzyme, [I] is the concentration of the inhibitor, and [EI] is the concentration of the enzyme-inhibitor complex formed by the reaction of the enzyme with the inhibitor. Unless otherwise specified, $K_i$ as used herein refers to the affinity between the inventive compounds and NAALADase. "$IC_{50}$" is a related term used to define the concentration or amount of a compound which is required to cause a 50% inhibition of the target enzyme.

"Ischemia" refers to localized tissue anemia due to obstruction of the inflow of arterial blood. Global ischemia occurs when blood flow to the entire brain ceases for a period of time, such as may result from cardiac arrest. Focal ischemia occurs when a portion of the brain is deprived of its normal blood supply, such as may result from thromboembolytic occlusion of a cerebral vessel, traumatic head injury, edema or brain tumor. Even if transient, both global and focal ischemia can produce widespread neuronal damage. Although nerve tissue damage occurs over hours or even days following the onset of ischemia, some permanent nerve tissue damage may develop in the initial minutes following cessation of blood flow to the brain Much of this damage is attributed to glutamate toxicity and secondary consequences of reperfusion of the tissue, such as the release of vasoactive products by damaged endothelium, and the release of cytotoxic products, such as free radicals and leukotrienes, by the damaged tissue.

"NAAG" refers to N-acetyl-aspartyl-glutamate, an important peptide component of the brain, with levels comparable to the major inhibitor neurotransmitter gamma-aminobutyric acid (GABA). NAAG is neuron-specific, present in synaptic vesicles and released upon neuronal stimulation in several systems presumed to be glutamatergic. Studies suggest that NAAG may function as a neurotransmitter and/or neuromodulator in the central nervous system, or as a precursor of the neurotransmitter glutamate.

"NAALADase" refers to N-acetylated α-linked acidic dipeptidase, a membrane-bound metallopeptidase which catabolizes NAAG to N-acetylaspartate (NAA) and glutamate:

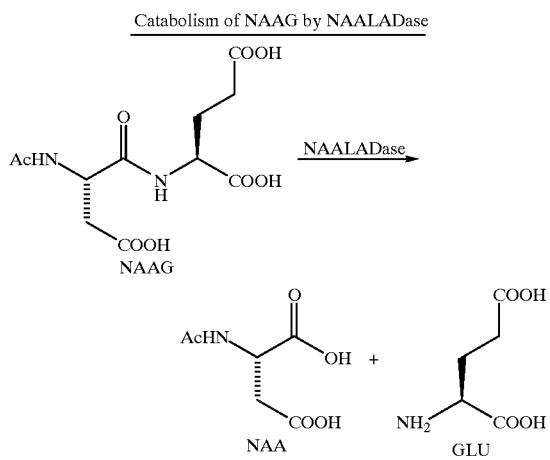

Catabolism of NAAG by NAALADase

NAALADase shows a high affinity for NAAG with a Km of 540 nM. If NAAG is a bioactive peptide, then NAALADase may serve to inactivate NAAG'S synaptic action. Alternatively, if NAAG functions as a precursor for glutamate, the primary function of NAALADase may be to regulate synaptic glutamate availability.

"Nervous function" refers to the various functions of the nervous system, which among other things provide an awareness of the internal and external environments of the body, make possible voluntary and reflex activities between the various structural elements of the organism, and balance the organism's response to environmental changes.

"Nervous insult" refers to any damage to nervous tissue and any disability or death resulting therefrom. The cause of nervous insult may be metabolic, toxic, neurotoxic, iatrogenic, thermal or chemical, and includes without limitation ischemia, hypoxia, cerebrovascular accident, trauma, surgery, pressure, mass effect, hemorrhage, radiation, vasospasm, neurodegenerative disease, neurodegenerative process, infection, Parkinson's disease, ALS, myelination/demyelination process, epilepsy, cognitive disorder, glutamate abnormality and secondary effects thereof. Currently, there is no known effective treatment for nervous tissue damage.

"Nervous tissue" refers to the various components that make up the nervous system, including without limitation neurons, neural support cells, glia, Schwann cells, vasculature contained within and supplying these structures, the central nervous system, the brain, the brain stem, the spinal cord, the junction of the central nervous system with the peripheral nervous system, the peripheral nervous system and allied structures.

"Neuroprotective" refers to the effect of reducing, arresting or ameliorating nervous insult, and protecting, resuscitating or reviving nervous tissue which has suffered nervous insult.

"Pathological gambling" is a condition characterized by a preoccupation with gambling. Similar to psychoactive substance abuse, its effects include development of tolerance with a need to gamble progressively larger amounts of money, withdrawal symptoms, and continued gambling despite severe negative effects on family and occupation.

"Pharmaceutically acceptable salt" refers to a salt of the inventive compounds which possesses the desired pharmacological activity and which is neither biologically nor otherwise undesirable. The salt can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. The basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Tourette's syndrome" refers to an autosomal multiple tic disorder characterized by compulsive swearing, multiple muscle tics and loud noises. Tics are brief, rapid, involuntary movements that can be simple or complex; they are stereotyped and repetitive, but not rhythmic. Simple tics, such as eye blinking, often begin as nervous mannerisms. Complex tics often resemble fragments of normal behavior.

"Treating" refers to:

(i) preventing a disease, disorder or condition from occurring in an animal which may be predisposed to the disease, disorder and/or condition but has not yet been diagnosed as having it;

(ii) inhibiting the disease, disorder or condition, i.e., arresting its development; and (iii) relieving the disease, disorder or condition, i.e., causing regression of the disease, disorder and/or condition.

In relation to drug dependence, "treating" refers to suppressing the psychologic addiction or physical tolerance to the drug of abuse, and relieving or preventing a withdrawal syndrome resulting from the drug dependence.

"Withdrawal syndrome" refers to a disorder characterized by untoward physical changes that occur when the drug is discontinued or when its effect is counteracted by a specific antagonist.

METHODS OF THE PRESENT INVENTION

The present invention relates to a method of synthesizing in non-racemic form a compound of formula I

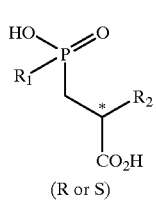

(R or S)

I which comprises asymmetrically reducing a compound of formula II

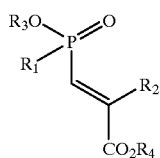

II wherein:
R$_1$, R$_2$, R$_3$ and R$_4$ are independently selected from the group consisting of hydrogen, C$_1$–C$_9$ straight or branched chain alkyl, C$_2$–C$_9$ straight or branched chain alkenyl, C$_3$–C$_8$ cycloalkyl, C$_5$–C$_7$ cycloalkenyl and Ar, wherein said R$_1$, R$_2$, R$_3$ and R$_4$ are independently unsubstituted or substituted with one or more substituent(s) independently selected from the group consisting of carboxy, C$_3$–C$_8$ cycloalkyl, C$_5$–C$_7$ cycloalkenyl, halo, hydroxy, nitro, trifluoromethyl, C$_1$–C$_6$ straight or branched chain alkyl, C$_2$–C$_6$ straight or branched chain alkenyl, C$_1$–C$_9$ alkoxy, C$_2$-C$_9$ alkenyloxy, phenoxy, benzyloxy, amino, and Ar; and Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl, benzyl and phenyl, wherein said Ar is unsubstituted or substituted with one or more substituent(s) independently selected from the group consisting of halo, hydroxy, nitro, trifluoromethyl, C$_1$–C$_6$ straight or branched chain alkyl, C$_2$–C$_6$ straight or branched chain alkenyl, C$_1$–C$_6$ alkoxy, C$_2$–C$_6$ alkenyloxy, phenoxy, benzyloxy, and amino.

In a preferred embodiment, R$_3$ and R$_4$ are tert-butyl.

In another preferred embodiment, R$_3$ and R$_4$ are hydrogen.

In a more preferred embodiment, R$_2$ is —(CH$_2$)$_2$COOH.

In an even more preferred embodiment, R$_1$ is selected from the group consisting of hydrogen, C$_1$–C$_4$ straight or branched chain alkyl, C$_2$–C$_4$ straight or branched chain alkenyl, C$_3$–C$_8$ cycloalkyl, C$_5$–C$_7$ cycloalkenyl, benzyl and phenyl, wherein said R$_1$ is unsubstituted or substituted with one or more substituent(s) independently selected from the group consisting of carboxy, C$_3$–C$_8$ cycloalkyl, C$_5$–C$_7$ cycloalkenyl, halo, hydroxy, nitro, trifluoromethyl, C$_1$–C$_6$ straight or branched chain alkyl, C$_2$–C$_6$ straight or branched chain alkenyl, C$_1$–C$_4$ alkoxy, C$_2$–C$_4$ alkenyloxy, phenoxy, benzyloxy, amino, benzyl, and phenyl.

In the most preferred embodiment, R$_1$ is phenyl.

Preferred compounds of formula I are selected from the group consisting of:
2-(phosphonomethyl)pentanedioic acid;
2-(phosphonomethyl)succinic acid;
2-[[(2-carboxyethyl)hydroxyphosphinyl]methyl] pentanedioic acid;
2-[(benzylhydroxyphosphinyl)methyl]pentanedioic acid;
2-[(phenylhydroxyphosphinyl)methyl]pentanedioic acid;
2-[[((hydroxy)phenylmethyl)hydroxyphosphinyl]methyl]-pentanedioic acid;
2-[(butylhydroxyphosphinyl)methyl]pentanedioic acid;
2-[[(3-methylbenzyl)hydroxyphosphinyl]methyl] pentanedioic acid;
2-[(3-phenylpropylhydroxyphosphinyl)methyl]pentanedioic acid;

2-[[(4-fluorophenyl)hydroxyphosphinyl]methyl] pentanedioic acid;
2-[(methylhydroxyphosphinyl)methyl]pentanedioic acid;
2-[(phenylethylhydroxyphosphinyl)methyl]pentanedioic acid;
2-[[(4-methylbenzyl)hydroxyphosphinyl]methyl] pentanedioic acid;
2-[[(4-fluorobenzyl)hydroxyphosphinyl]methyl] pentanedioic acid;
2-[[(4-methoxybenzyl)hydroxyphosphinyl]methyl] pentanedioic acid;
2-[[(3-trifluoromethylbenzyl)hydroxyphosphinyl]methyl] pentanedioic acid;
2-[[(2-fluorobenzyl)hydroxyphosphinyl]methyl] pentanedioic acid;
2-[[(pentafluorobenzyl) hydroxyphosphinyl]methyl] pentanedioic acid;
2-[[(phenylprop-2-enyl) hydroxyphosphinyl methyl] pentanedioic acid;
2-[[(aminomethyl) hydroxyphosphinyl]methyl]pentanedioic acid;
2-[[(aminoethyl)hydroxyphosphinyl]methyl]pentanedioic acid;
2-[ [(aminopropyl)hydroxyphosphinyl]methyl]pentanedioic acid; and pharmaceutically acceptable salts and hydrates thereof.

The most preferred compound of formula I is 2-[(phenylhydroxyphosphinoyl) methyl]pentanedioic acid, and the most preferred compound of formula II is di(tert-butyl) 2-{[tert-butyloxy (E)-1-phenylphosphinoyl] methylidene}pentanedioate.

Di(tert-butyl) 2-{[tert-butyloxy (E)-1-phenylphosphinoyl]methylidene}pentanedioate may be synthesized by:

(i) contacting tetrabutylammonium fluoride trihydrate and hexamethylphosphoroamide with di(tert-butyl) 2-bromo-2-(bromomethyl)pentanedioate to form di(tert-butyl) 2-(E)-1-bromomethylidene) pentanedioate; and (ii) contacting said di(tert-butyl) 2-(E)-1-bromomethylidene) pentanedioate with tert-butyl phenylphosphinic acid, triethyl amine, and dichlorobis [triphenylphosphine]palladium.

The reducing step of the inventive method may comprise contacting said compound of formula II with an optically active chiral catalyst and a source of H$_2$ to form a mixture, then contacting said mixture with an acidic solution. Preferably, the chiral catalyst is chloro(1,5-cyclooctadiene) rhodium (I) dimer, the source of H$_2$ is triethylammonium formate, and the acidic solution comprises trifluoroacetic acid and dichloromethane. However, the present invention contemplates using other suitable optically active chiral catalysts, sources of H$_2$, and acidic solutions known in the art.

Alternatively, the reducing step may comprise contacting said compound of formula II with trifluoroacetic acid and dichloromethane to form a mixture, then contacting said mixture with (+)-2,3-O-isopropylidene-2,3-dihydroxy-1,4-bis(diphenyl-phosphino)butane (DIOP), chloro(1,5-cyclo-octadiene) rhodium (I) dimer, anhydrous dimethyl sulfoxide and triethylammonium formate.

Enantiomer-enriched mixtures of hydroxyphosphinyl derivatives can be readily prepared using the asymmetric reduction syntheses depicted below in Scheme I.

Scheme I

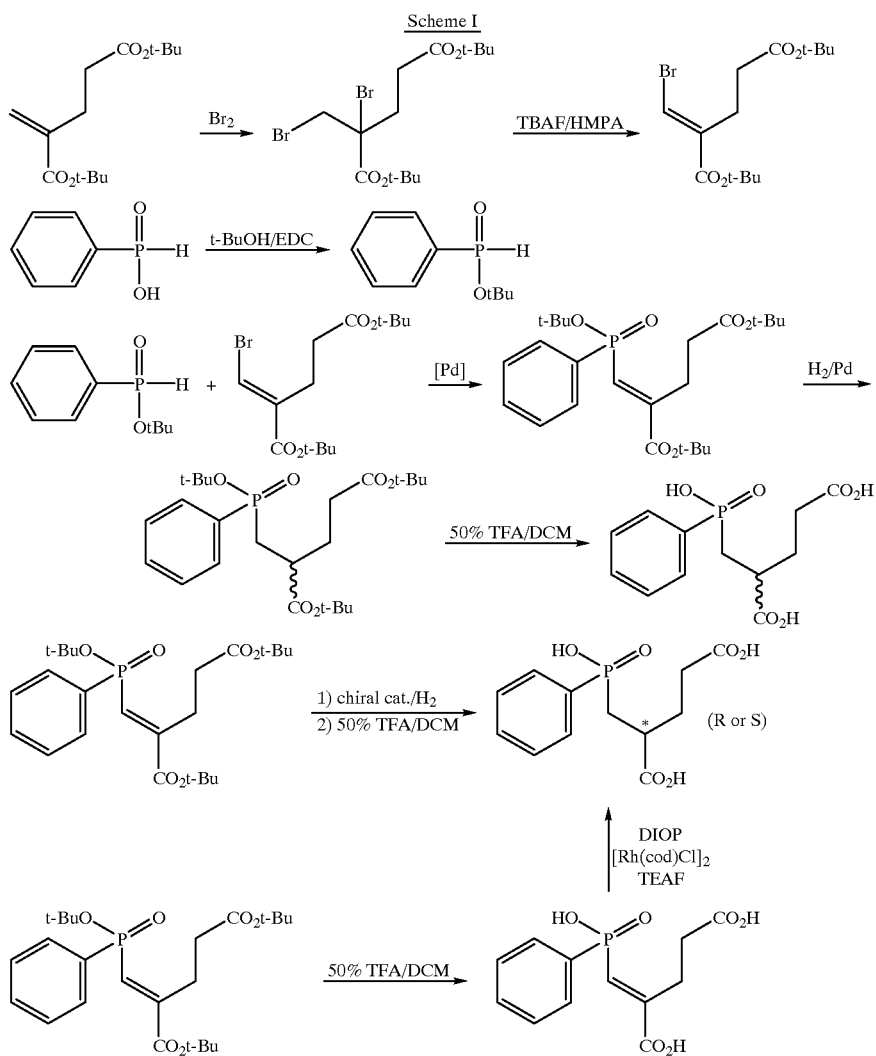

Less enantiomer-enriched (more racemic) mixtures of hydroxyphosphinyl derivatives can be synthesized using standard techniques of organic chemistry, utilizing the general synthetic pathways depicted below in Schemes II–VIII. Precursor compounds can be prepared by methods known in the art, such as those described by Jackson et al., *J. Med. Chem.*, Vol. 39, No. 2, pp. 619–622 (1996) and Froestl et al., *J. Med. Chem.*, Vol. 38, pp. 3313–3331 (1995).

Scheme II

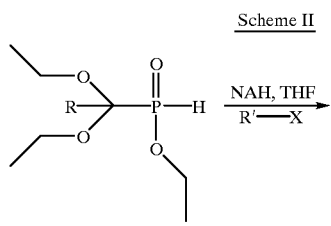

-continued

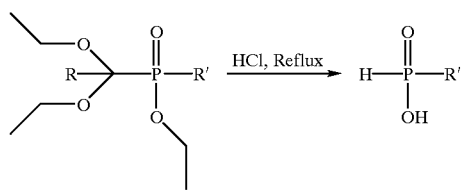

Methods of substituting the R group are known in the art. Additional methods of synthesizing phosphinic acid esters are described in *J. Med. Chem.*, Vol. 31, pp. 204–212 (1988), and set forth below in Scheme III.

Scheme III

Method A

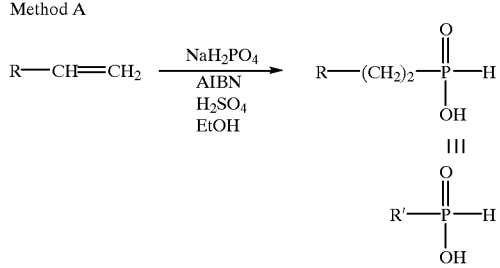

| | | | |
|---|---|---|---|
| A. | R' = (CH$_2$)$_3$Ph | H. | R' = n-C$_7$H$_{15}$ |
| B. | (CH$_2$)$_4$Ph | I. | n-C$_8$H$_{17}$ |
| C. | (CH$_2$)$_5$Ph | J. | n-C$_9$H$_{19}$ |
| D. | (CH$_2$)$_4$(P—F—Ph) | K. | CH$_2$CHCH$_3$C$_4$H$_9$ |
| E. | (CH$_2$)$_4$-(3-pyridyl) | L. | CH$_2$(CH$_3$)C(CH$_3$)$_2$ |
| F. | n-C$_5$H$_{11}$ | | |
| G. | n-C$_6$H$_{13}$ | | |

Method B

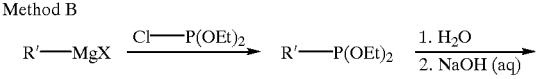

N. R' = n-C$_4$H$_9$
O. CHCH$_3$C$_5$H$_{11}$

Starting with the aforementioned phosphinic acid esters, there are a variety of routes for preparing the compounds of formula I. For example, a general route has been described in *J. Med. Chem.*, Vol. 39, pp. 619–622 (1996), and is set forth below in Scheme IV.

Scheme IV

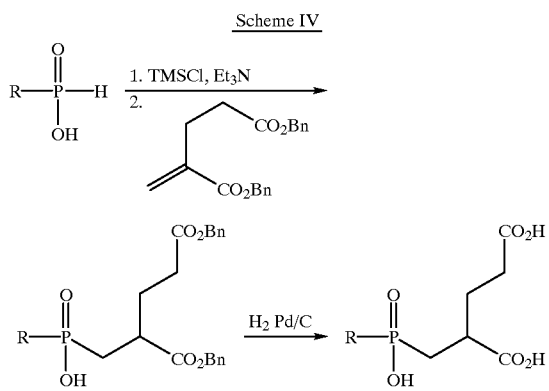

Other routes for preparing the compounds of formula I are set forth below in Scheme V and Scheme VI. Scheme V and Scheme VI show the starting material as a phosphinic acid derivative and the R group as any reasonable chemical substituent including without limitation the substituents listed in Scheme III and throughout the specification.

Scheme V

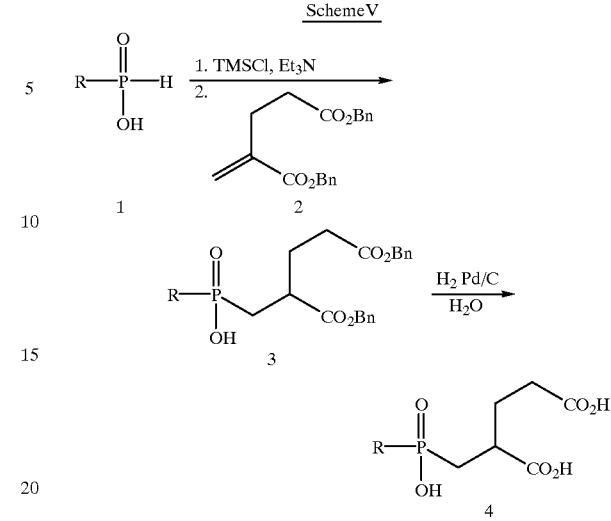

Scheme VI

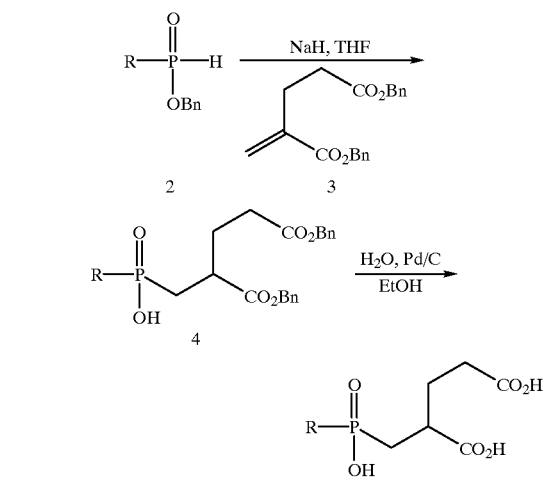

Another route for preparing the compounds of formula I allows for aromatic substitution at R$_1$, and is set forth below in Scheme VII.

Scheme VII

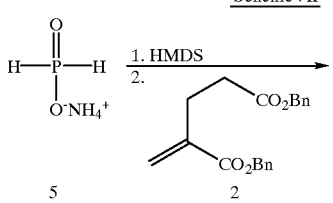

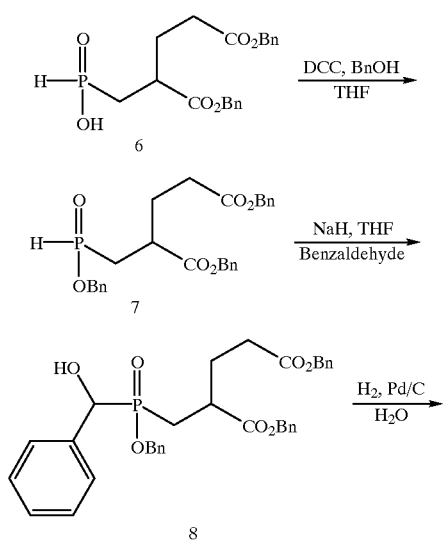
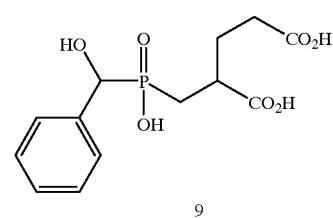
Another route for preparing the compounds of formula I allows for aromatic substitution at the $R_2$ position, and is set forth below in Scheme VIII.
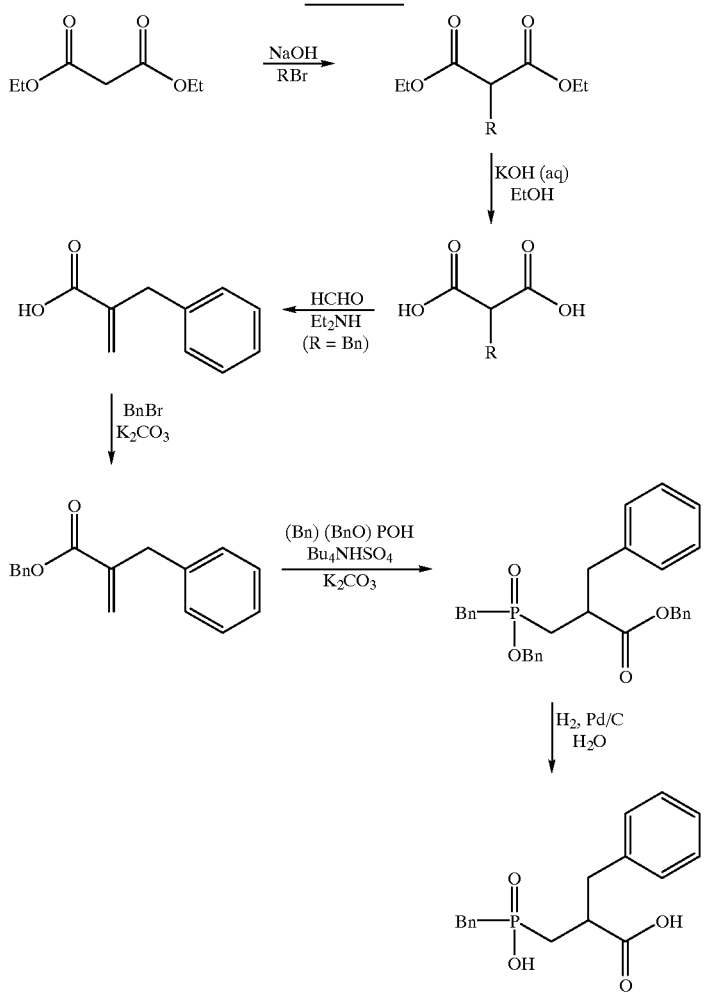

COMPOUNDS OF THE PRESENT INVENTION

The present invention further relates to an intermediate for preparing the enantiomer-enriched hydroxyphosphinyl derivatives of formula I. Specifically, the intermediate is a compound of formula II

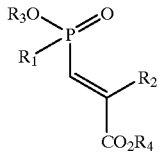

II or a pharmaceutically acceptable salt or hydrate thereof, wherein:

$R_1$, $R_2$, $R_3$ and $R_4$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_1$, $R_2$, $R_3$ and $R_4$ are independently unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, and Ar; and Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl, benzyl and phenyl, wherein said Ar is unsubstituted or substituted with one or more substituent(s) independently selected from the group consisting of halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, and amino.

In a preferred embodiment, $R_3$ and $R_4$ are tert-butyl.

In another preferred embodiment, $R_3$ and $R_4$ are hydrogen.

In a more preferred embodiment, $R_2$ is —$(CH_2)_2COOH$.

In an even more preferred embodiment, $R_1$ is selected from the group consisting of hydrogen, $C_1$–$C_4$ straight or branched chain alkyl, $C_2$–$C_4$ straight or branched chain alkenyl, $C_3$–$C_8$ cycloalkyl, $C_5$–$C_7$ cycloalkenyl, benzyl or phenyl, wherein said $R_1$ is unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, benzyl, and phenyl.

In the most preferred embodiment, $R_1$ is phenyl.

Preferred compounds of formula II are di(tert-butyl) 2-{[tert-butyloxy (E)-1- phenyl-phosphinoyl]methylidene}-pentanedioate and 2-{[hydroxy (E)-1-phenylphosphinoyl]methylidene}pentanedioic acid.

EXAMPLES

The following examples are illustrative of the present invention and are not intended to be limitations thereon.

EXAMPLE 1

Asymmetric synthesis of (R)-(–)-2-[(phenylhydroxyphosphinovl)methyl]pentanedioic acid Synthesis of di(tert-butyl) 2-bromo-2-(bromomethyl)-pentanedioate

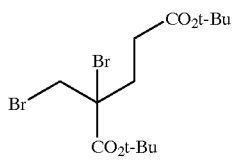

A 50 ml three-necked round-bottomed flask fitted with a reflux condenser, a 60 ml pressure-equalizing addition funnel, a magnetic stirring bar, an argon inlet and an oil bubbler is charged with di(tert-butyl) 2-methylenepentanedioate (2.56 g, 10 mmol) and anhydrous carbon tetrachloride (10 ml) The reaction flask is stoppered and argon is flown into the flask while the addition funnel is charged with a solution of bromine (0.54 ml, 10.5 mmol) in carbon tetrachloride (5 ml). The flask is placed in an oil bath and heated to gentle reflux under magnetic stirring. Then the bromine:carbon tetrachloride solution is added dropwise until a deep orange-brownish color persists in the reaction mixture. The final reaction mixture is cooled, transferred to a separatory funnel, washed with a 5% aqueous solution of sodium thiosulfate (2x), water (2x), and brine (2x). The organic phase is then dried over anhydrous magnesium sulfate, filtered and concentrated under reduced pressure to afford a pale yellow oil.

$^1$H NMR (CDCl$_3$+0.03% TMS) (units in ppm relative to TMS): 1.47 (s, 9H), 1.51 (s, 9H), 2.32–2.48 (ml 2H), 2.55–2.63 (m, 2H), 3.67 (d, 1H), 4.12 (d, 1H).

Synthesis of di(tert-butyl) 2-[(E)-1-bromomethylidene) pentanedioate

A 50 ml three-necked round-bottomed flask fitted with a magnetic stirring bar, an argon inlet and an oil bubbler is charged with tetrabutylammonium fluoride trihydrate (3.95 g, 12.5 mmol) and hexamethylphosphoro-amide (10 ml) under an argon atmosphere. The reaction flask is cooled to 0° C. by using an ice-water bath and the reaction mixture is magnetically stirred until it became homogeneous Then di(tert-butyl) 2-bromo-2-(bromo-methyl)pentanedioate (10 mmol) is added dropwise to the reaction mixture via syringe over a period of 30 minutes. The reaction mixture is further stirred for 1 hour at 0° C. and then allowed to warm up to room temperature overnight. The final brown reaction mixture is cooled by means of an ice-water bath and quenched with a 2 N aqueous solution of sulfuric acid and then extracted with hexanes. The extracts are combined, washed with water until the pH of the aqueous layer is neutral, dried over anhydrous magnesium sulfate, filtered and concentrated under reduced pressure. The residue was distilled under high vacuum to afford a colorless oil.

$^1$H NMR (CDCl$_3$+0.03% TMS) (units in ppm relative to TMS) 1.45 (s, 9H), 1.49 (s, 9H), 2.35 (m, 2H), 2.66 (m, 2H), 7.43 (s, 1H).

Synthesis of tert-butyl phenylphosphinate

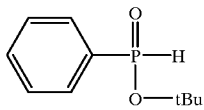

A 100 ml single-necked round-bottomed flask fitted with a magnetic stirring bar is charged with phenylphosphinic acid (2.84 g, 20 mmol) and tert-butyl alcohol (1.63 g, 22 mmol), and dichloromethane (60 ml). Then 1-(3-dimethylaminopropyl)-3-ethylcarbodiimide hydrochloride (7.67 g, 40 mmol) is added under stirring and the reaction mixture is magnetically stirred for 90 minutes at room temperature. The final colorless reaction mixture is transferred to a separatory funnel, washed twice with 2 N aqueous HCl, dried over anhydrous magnesium sulfate, filtered and concentrated under reduced pressure to afford an oil residue. This residue was then chromatographed over silica gel using ethyl acetate to afford a pale yellow oil (Rf=0.39).

$^1$H NMR (CDCl$_3$+0.03% TMS) (units in ppm relative to TMS): 1.5 (s, 9H), 7.37–7.43 (m, 2H), 7.47 (m, 1H), 7.55–7.59 (m, 2H).

Synthesis of di(tert-butyl) 2-{[tert-butyloxy (E)-1-phenylphosphinoyl]methylidene}pentanedioate

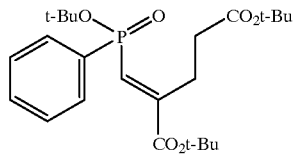

A screw-capped culture tube is charged with di (tert-butyl) 2-[(E)-1-bromomethylidene)pentanedioate, tert-butyl phenylphosphinic acid, triethyl amine, and 5% mol dichlorobis [triphenylphosphine]palladium. The tube is flushed with argon for 1 minute, capped and heated in a heating block at 100–105° C. for 1 hour. The tube is then allowed to cool to room temperature, ethyl acetate is added to the tube, the mixture is filtered, and the precipitate rinsed with ethyl acetate. The combined filtrates are concentrated under reduced pressure and the obtained residue is chromatographed over silica gel using a 3:1 solution of dichloromethane:ethyl acetate to afford a pale yellow oil.

$^1$H NMR (CDCl$_3$+0.03% TMS) (units in ppm relative to TMS): 1.33 (s, 9H), 1.40 (s, 18H), 2.05–2.12 (m, 1H), 2.23–2.29 (m, 1H), 2.80–2.86 (m, 2H), 6.72–6.76 (d, 1H), 7.38–7.41 (m, 2H), 7.43(m, 1H), 7.72–7.77 (m, 2H). 31P NMR: 24.37.

Synthesis of di(tert-butyl) 2-(tert-butyloxy-1-phenylphosphinoylmethyl)-pentanedioate

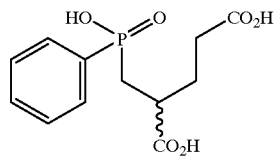

A hydrogenation bottle is charged with di(tert-butyl) 2-{[tert-butyloxy (E)-1-phenylphosphinoyl]-methylidene} pentanedioate and dissolved in ethyl acetate. The solution is then hydrogenated over 10% palladium on carbon at 40 psi for 4 days. The final reaction mixture is filtered through a silica gel pad eluting the product with ethyl acetate. The combined filtrates are evaporated under reduced pressure to afford a colorless oil.

$^1$H NMR (CDCl$_3$+0.03% TMS) (units in ppm relative to TMS) 1.28 (s, 9H), 1.33 (s, 9H), 1.36 (s, 9H), 1.8–1.96 (m, 3H), 2.10–2.25 (m, 3H), 2.63 (m, 1H), 7.36–7.41 (m, 3H), 7.68–7.73(m, 2H). 31P NMR: 38.16.

Synthesis of 2-[(phenylhydroxyohosphinovl)methyl]-pentanedioic acid

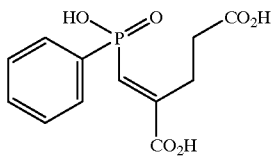

Di(tert-butyl) 2-{[tert-butyloxy-1-phenyl-phosphinoyl)methyl]pentanedioic acid is treated with a 50% solution of trifluoroacetic acid:dichloro-methane for 2 hours at room temperature. The final reaction mixture is reduced under reduced pressure, the residue is taken in a 50% solution of acetonitrile:water and freeze-dried.

$^1$H NMR (dimethyl sulfoxide-d6+0.03% TMS) (units in ppm relative to TMS): 1.67–1.73 (m, 1H), 1.79–1.82 (m, 2H), 2.10–2.16 (m, 3H), 2.48–2.50 (m, 1H), 7.48–7.55 (m, 3H), 7.68–7.73 (m, 2H). 31P NMR: 35.89.

Synthesis of 2-{[hydroxy (E)-1-phenylphosphinoyl]-methylidene}pentanedioic acid

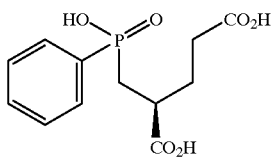

Di(tert-butyl) 2-{[tert-butyloxy (E)-1-phenyl-phosphinoyl]methylidene}pentanedioic acid is treated with a 50% solution of trifluoroacetic acid:dichloromethane at room temperature. The final reaction mixture is concentrated under reduced pressure to afford a gray solid.

$^1$H NMR (dimethyl sulfoxide-d6+0.03% TMS) (units in ppm relative to TMS): 2.26–2.31 (m, 2H), 2.88–2.92 (m, 2H), 6.80–6.85 (d, 1H), 7.52–7.66 (m, 3H), 7.77–7.82 (m, 2H). 31P NMR: 21.82.

Asymmetric synthesis of (R)-(−)-2-[(phenylhydroxyphosphinoyl)methyl]pentanedioic acid A single-necked round-bottomed flask fitted with a magnetic stirring bar is charged with 2-{[hydroxy (E) -1-phenylphosphinoyl]-methylidene}pentanedioic acid (0.6 g, 2.11 mmol), (+)-2,3-O-isopropylidene-2,3-dihydroxy-1,4-bis(diphenylphosphino)butane (DIOP) (0.043 g, 0.0826 mmol), chloro(1,5-cyclooctadiene)rhodium (I) dimer (0.088 g, 0.178 mmol) and anhydrous dimethyl sulfoxide (3.5 ml). This mixture is stirred at room temperature for 30 minutes, triethylammonium formate (3 ml) is then added dropwise, and the reaction mixture is stirred at room temperature for 24 hours. The final reaction mixture is poured into water and extracted with ethyl acetate. The combined extracts are dried over anhydrous sodium sulfate, filtered and concentrated under reduced pressure. The obtained residue is then chromatographed over silica gel using a 3:1 solution of hexanes:ethyl acetate to afford the desired enantiomerically-rich product. A polarimetric analysis of an aqueous solution of the final product confirms that the final compound is obtained enantiomerically enriched.

Di(tert-butyl) 2-{[tert-butyloxy (E)-1-phenylphosphinoyl]-methylidene}pentanedioate could also be asymmetrically reduced in the presence of a chiral catalyst to afford reduced material in a racemic-free way with a high enantiomeric excess of the desired enantiomer. Further treatment with a 50% solution of trifluoroacetic acid:dichloromethane would remove the tert-butyl groups to provide the final racemic-free desired material.

The invention being thus described, it will be obvious that the same may be varied in many ways. Such variations are not to be regarded as a departure from the spirit and scope of the invention and all such modifications are intended to be included within the scope of the following claims.

We claim:

1. A method of synthesizing in non-racemic form a compound of formula I

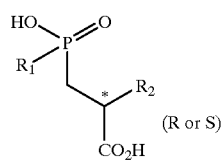

which comprises asymmetrically reducing a compound of formula II

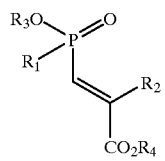

wherein:
  $R_1$, $R_2$, $R_3$ and $R_4$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, provided that $R_2$ is not hydrogen wherein said $R_1$, $R_2$, $R_3$ and $R_4$ are independently unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, and Ar; and
  Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl, benzyl and phenyl, wherein said Ar is unsubstituted or substituted with one or more substituent(s) independently selected from the group consisting of halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, and amino;
  wherein said reducing comprises contacting said compound of formula II with an optically active chiral catalyst.

2. The method of claim 1, wherein $R_3$ and $R_4$ are tert-butyl.

3. The method of claim 1, wherein $R_3$ and $R_4$ are hydrogen.

4. The method of claim 1, wherein $R_2$ is —$(CH_2)_2COOH$.

5. The method of claim 4, wherein $R_1$ is selected from the group consisting of hydrogen, $C_1$–$C_4$ straight or branched chain alkyl, $C_2$–$C_4$ straight or branched chain alkenyl, $C_3$–$C_8$ cycloalkyl, $C_5$–$C_7$ cycloalkenyl, benzyl and phenyl, wherein said $R_1$ is unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, benzyl, and phenyl.

6. The method of claim 5, wherein $R_1$ is phenyl.

7. The method of claim 1, wherein said reducing further comprises contacting said compound of formula II with a source of $H_2$ to form a mixture, then contacting said mixture with an acidic solution.

8. The method of claim 7, wherein said optically active chiral catalyst is chloro(1,5-cyclooctadiene) rhodium (I) dimer.

9. The method of claim 7, wherein said source of $H_2$ is triethylammonium formate.

10. The method of claim 7, wherein said acidic solution comprises trifluoroacetic acid and dichloromethane.

11. The method of claim 7, wherein said reducing comprises contacting said compound of formula II with trifluoroacetic acid and dichloromethane to form a mixture, then contacting said mixture with (+)-2,3-O-isopropylidene-2,3-dihydroxy-1,4-bis(diphenyl-phosphino)butane (DIOP), chloro(1,5-cyclo-octadiene)rhodium (I) dimer, anhydrous dimethyl sulfoxide and triethylammonium formate.

12. The method of claim 1, wherein the compound of formula I is 2-[(phenylhydroxyphosphinoyl)methyl]-pentanedioic acid and the compound of formula II is di(tert-butyl) 2-{[tert-butyloxy (E)-1-phenylphosphinoyl] methylidene}pentanedioate.

13. The method of claim 12, which further comprises synthesizing the compound of formula II by
  (i) contacting tetrabutylammonium fluoride trihydrate and hexamethylphosphoroamide with di(tert-butyl) 2-bromo-2-(bromomethyl)pentanedioate to form di(tert-butyl) 2-(E)-1-bromomethylidene) pentanedioate; and
  (ii) contacting said di(tert-butyl) 2-(E)-1-bromomethylidene) pentanedioate with tert-butyl phenylphosphinic acid, triethyl amine, and dichlorobis[triphenylphosphine]palladium.

* * * * *